(12) United States Patent
Keren

(10) Patent No.: US 8,038,965 B2
(45) Date of Patent: Oct. 18, 2011

(54) DIAGNOSTIC KIT

(75) Inventor: Tomer Keren, Rishon Le Zion, IL (US)

(73) Assignee: Alere Switzerland GmbH, Zug (CH)

( * ) Notice: Subject to any disclaimer, the term of this patent is extended or adjusted under 35 U.S.C. 154(b) by 629 days.

(21) Appl. No.: 11/806,171

(22) Filed: May 30, 2007

(65) Prior Publication Data
US 2008/0299648 A1 Dec. 4, 2008

(51) Int. Cl.
*B01L 3/00* (2006.01)
*B01L 99/00* (2006.01)

(52) U.S. Cl. ........ 422/500; 422/401; 422/402; 422/411; 422/5; 436/514; 436/164; 436/169

(58) Field of Classification Search ............. 436/514
See application file for complete search history.

(56) References Cited

U.S. PATENT DOCUMENTS

| | | | | |
|---|---|---|---|---|
| 5,869,003 A * | 2/1999 | Nason | | 422/58 |
| 6,669,908 B2 * | 12/2003 | Weyker et al. | | 422/58 |
| 7,098,040 B2 * | 8/2006 | Kaylor et al. | | 436/514 |

\* cited by examiner

*Primary Examiner* — Sally Sakelaris
(74) *Attorney, Agent, or Firm* — Foley Hoag LLP

(57) ABSTRACT

The present invention relates to a diagnostic kit and more specifically to a self contained diagnostic kit providing analysis of a sample by a sample collectin element and an immunochromatography test strip.

9 Claims, 5 Drawing Sheets

DIAGNOSTIC KIT

BACKGROUND OF THE INVENTION

1. Field of the Invention

The present invention generally relates to a diagnostic kit and more specifically to a self contained diagnostic kit providing analysis of a sample by a sample collecting element and an immunochromatography test strip.

2. Discussion of the Related Art

Flow test strips are most commonly used for the last thirty years. The test strips are used for the specific qualitative or semi-quantitative detection of many analytes including antigens, antibodies, and even the products of nucleic acid amplification tests. One or several analytes can be tested for simultaneously on the same strip. Urine, saliva, serum, plasma, or whole blood can be used as samples. Extracts of patient exudates or fluids have also been successfully used.

Test sensitivity can be quite good. For example, hepatitis B surface antigen (HBsAg) test strips have claimed a sensitivity of 1.0 ng HBsAg/ml or less. Test specificity can also be very high. The tests use colloidal gold, dye, or latex bead conjugates to generate signal. The assembled strips are dried and packaged, making them stable for months when properly protected from moisture and excessive heat.

To perform the test, a sample either used alone or with an extraction reagent or a running buffer is placed on the sample pad on one end of the strip. The signal reagent is solubilized and binds to the antigen or antibody in the sample and moves through the membrane by capillary action. If specific analyte is present, the signal reagent binds to it, and a second antibody or antigen-immobilized as a line in the nitrocellulose then captures the complex. If the test is positive, a pink/purple line develops. Once the specimen is added, the tests can be left unattended until they are read. The tests can be run individually or in limited-size batches. Results can usually be read in 5 to 15 minutes. All tests include an internal procedural control line that is used to validate the test result. Appearance of two lines, therefore, indicates a positive result, while a negative test produces only one line.

Diagnosis of certain conditions at the oral, genital and rectal cavities (i.e Candida, Bacterial Vaginosis, colon cancer, HPV) require a sample taken by a swab or other collecting applicators before testing for the analyte using test strips. Collecting a sample is followed by an action aimed to preserve the sample from being contaminated and to keep sample's qualities (e.g. stability and arrangement of all components). Preserving a sample can be secured by placing the sample in a sterile container, or alternatively, placing the sample within a preserving liquid. Preserving sample after collecting it is necessary because the diagnosis of analytes within sample is not done immediately after sample's collection. Moreover, analysis of samples using test strips is usually performed not on the site of sample collection. The next step is placing the sample on a sample pad on one end of the strip. Furthermore, analyzing a sample with a test strip often requires the placing of the sample within an extraction reagent or running buffer, which is placed on the sample pad. Placing a sample on a sample pad requires appropriate training. Consequently, sample collection is performed by personnel other than the personnel performing the analysis of the sample. Naturally, due to different causes (e.g. misplacement and swapping of samples, unsuitable conditions) the time and distance intervals jeopardize the accuracy of the diagnosis. Hence, there is a need for a diagnosis kit enabling accurate on-site analysis of the sample.

Recent prior art discloses a diagnostic kit having a diagnostic strip placed within a tubular container. The kit requires first the placing of a specimen on swab tip within the tubular container, and followed by placing a removable cap that contains a reagent. Then, adding the reagent for initiating an analysis of the specimen. The requirement to add reagent to the tubular container requires concentration and accuracy performed preferably by experienced laboratory staff for a successful diagnosis. Furthermore, adding the reagent will occur sometime after the collection of the sample and usually at remote location from the sample collecting location rather than immediately after collecting a sample. Thus the prior art does not disclose a self contained diagnostic kit due to the fact that additional action is required after the specimen is collected and inserted in tubular container.

Furthermore, there are ever increasing requirements of public health authorities worldwide aiming to provide simple and accurate test kits for self use by layman. For example, the U.S. Clinical Laboratory Improvement Amendments of 1988 (CLIA) law specified that laboratory requirements be based on the complexity of the test performed and established provisions for categorizing a test as waived. Tests may be waived from regulatory oversight if they meet certain requirements established by the statute. Thus, On Feb. 28, 1992, regulations were published to implement CLIA. In the regulations, waived tests were defined as simple laboratory examinations and procedures that are cleared by the Food and Drug Administration (FDA) for home use; employ methodologies that are so simple and accurate as to render the likelihood of erroneous results negligible; or pose no reasonable risk of harm to the patient if the test is performed incorrectly.

Therefore there is a need to provide a completely self contained diagnostic kit. Furthermore, there is a need to provide a diagnostic kit that does not require special training for initiating analysis after insertion of sample. There is a need to provide a simple constructed self contained diagnostic kit. The above advantages as well as other are included in various embodiments of the disclosed invention.

SUMMARY OF THE PRESENT INVENTION

The present invention relates to a self contained diagnostic kit for analysis of samples. The diagnostic kit provides that subsequent to inserting a sample to the diagnostic kit an analysis of the sample initiates. One aspect of the present invention discloses a diagnostic kit for self analysis of at least one sample. The kit comprises a housing and at least one analysis strip unit, the analysis strip unit is positioned within the housing, the strip unit comprises a receptacle with an opening enabling initiation of analysis of the sample, and a flow strip comprising a sampling wick at one end of the flow strip. The sampling wick is adjacent to the receptacle. The receptacle can comprise a reagent. The analysis strip unit is structured to initiate analysis subsequent to contact with the sample. The analysis result of the analysis strip unit is visible. The diagnostic kit further comprises a sampling unit comprising a sampling element adapted to collect the sample. The sampling unit is removable from the housing. The sampling unit is adapted to reentered to the housing. The sampling unit is adapted to be received by the analysis strip unit. The sampling element is adapted to be received by the receptacle. The sampling element comprises a swab. The swab comprises at least one of the following materials, nylon, rayon, Dacron, cotton or any other materials. The sampling unit comprises a first end comprising the sampling element and a second end comprising a rod. The sampling unit comprises a rod wherein the rod comprises a first end adjacent to sampling element, and a second end having a plug. The plug substantially separates the analysis strip unit within the housing. The diagnostic kit can comprise one or more separators. The separator is adapted to aid defining at least two zones within the housing. The zone can comprise part of the analysis strip unit. One or more zones are adapted to enable removing the sampling unit out from the zone and to limit reentering the sampling unit to the zone. The sampling wick is adjacent to the opening of the receptacle. The sampling wick is adapted to be inserted to receptacle subsequent to the insertion of the sampling element to the receptacle. The analysis strip unit within the diagnosis kit is adapted to initiate analysis of the sample subsequently to the insertion of the sampling wick in the receptacle. The receptacle comprises a buffer, an extraction fluid, a combination thereof and the like. The receptacle is adapted to receive the sample. The opening of the receptacle is covered with a foil, which can be made penetrable.

According to a further aspect of the invention a diagnostic kit for self analysis of at least one sample is disclosed, the kit comprising a housing, a sample unit comprising a sampling element for collecting a sample and entering the sample to the housing, and an analysis strip unit, the analysis strip unit is positioned within the housing, the strip unit comprises a receptacle with an opening enabling initiation of analysis of the sample, and a flow strip comprising a sampling wick at one end of the flow strip, wherein the sampling wick is adjacent to the receptacle. The diagnostic kit further comprising at least one separator. The separator is adapted to aid defining two or more zones within the housing. The first zone comprises at least part of the analysis strip unit, and at least one second zone comprising a sample unit. The second zone is adapted to enable removing of sample unit from the second zone and limiting reentering of the sample unit to the second zone. The sampling wick is adjacent to the opening of the receptacle. The sampling wick is adapted to be inserted partially within the receptacle subsequent to the insertion of the sampling element within the receptacle. The analysis strip unit is adapted to initiate analysis of the sample subsequently to the insertion of at least a part of the sampling wick with the receptacle. The sampling element can be a swab. The receptacle comprises at least one reagent for extracting the sample from the sampling element.

BRIEF DESCRIPTION OF THE DRAWINGS

The present invention will be understood and appreciated more fully from the following detailed description taken in conjunction with the drawings in which.

DETAILED DESCRIPTION OF THE PREFERRED EMBODIMENT

The present invention provides a self contained diagnostic kit. The diagnostic kit comprises of a housing, and an analysis strip unit comprising a buffer reservoir that is positioned within the housing. The analysis of the sample can be initiated subsequently to the insertion of the sample to the housing. According to one exemplary embodiment the diagnostic kit comprises further a sampling unit having a sampling element such as a swab for collecting a sample and inserting the sample to the housing. Thus, subsequent to inserting the swab to the housing the analysis is initiated without further requirement of additional reagents or buffer.

According to another exemplary embodiment the diagnostic kit comprises further a sample receptacle that subsequent to the contact with the sample initiates its analysis. An embodiment of the invention is described below.

Figure 1A:
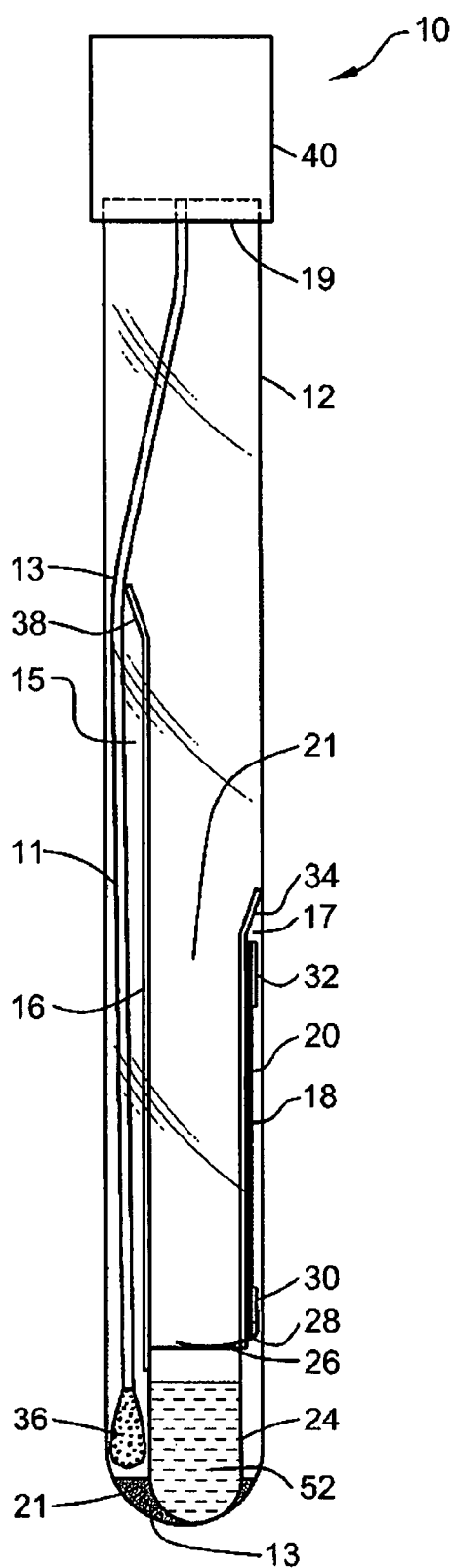
FIGS. 1A, 1B are front and side views, respectively, of a diagnostic kit according to the present invention wherein an analysis strip unit and sampling unit are initially inserted within housing.
Figure 1B:
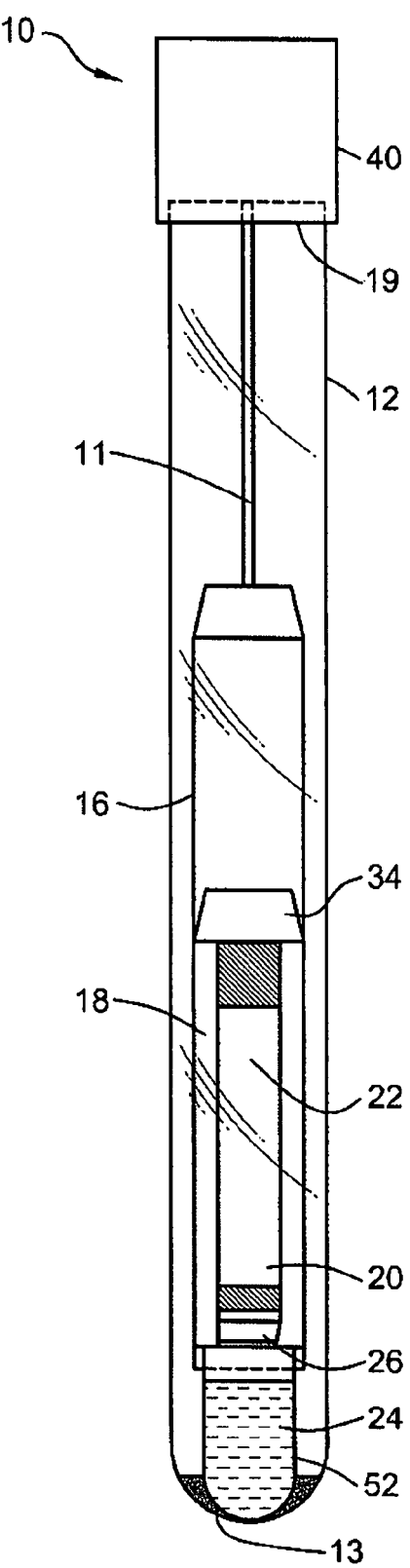
Figure 4A:
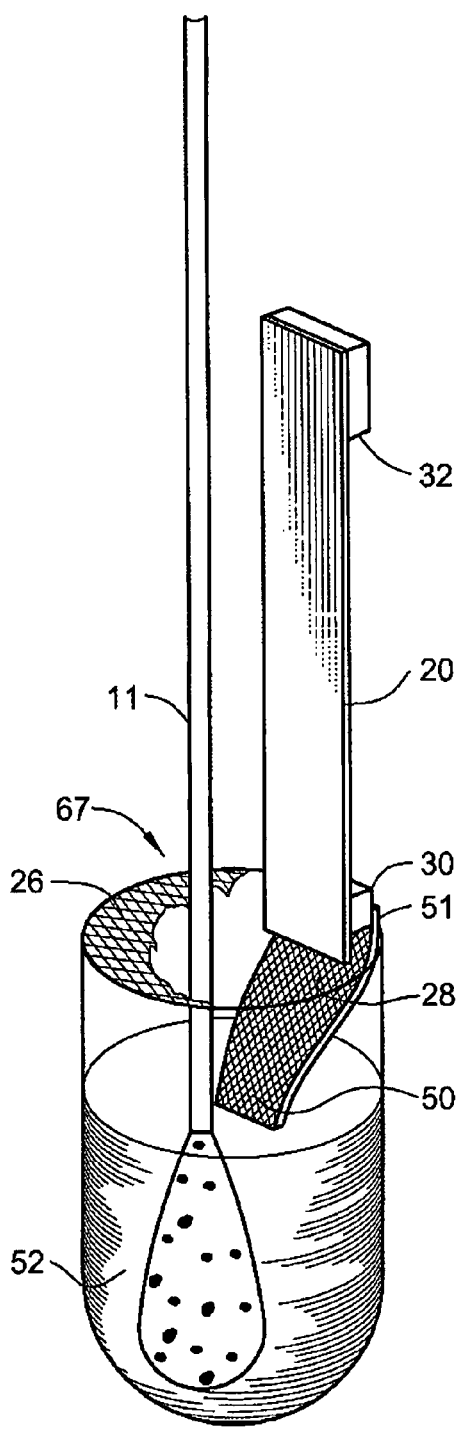
FIGS. 4A, 4B are perspective close up views of sampling element before and after inserting receptacle element, respectively, without showing the separators, according to the embodiment of FIG. 1A.
Figure 4B:
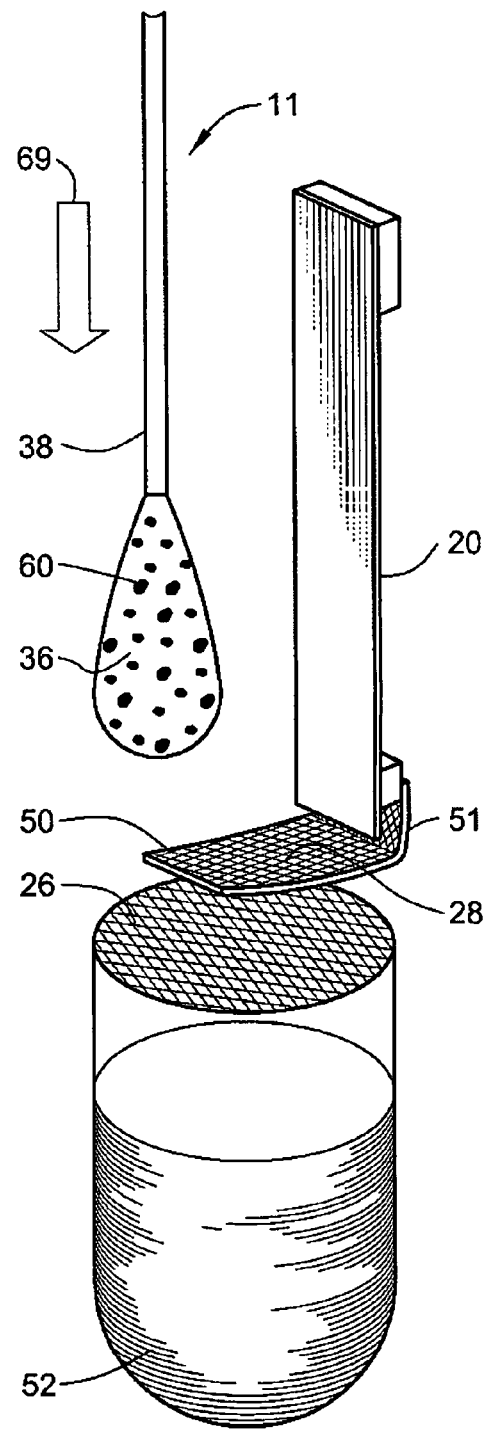

FIGS. 1A, 1B show a diagnostic kit 10 comprising a housing 12 with an analysis strip unit 20 and sampling unit 11, both positioned within said housing. Housing 12 is a tubular shape and comprises a first open end 17, used for insertion of samples in the housing, and second closed end 19, used for placing analysis strip unit 20. Housing 12 is made from transparent glass but can be made from any substantially inert and chemical resistant materials that are durable for the reagents used within an analysis. Thus, housing can be fabricated from different polymers e.g. polystyrene, polycarbonate, ceramic materials, a combination thereof and the like. The housing can be fabricated from transparent materials or opaque materials as far as part of the analysis strip unit 20 (i.e. lateral flow strip membrane 22 presenting the analysis results is depicted below) can be viewed on the outside of housing 12. Analysis strip unit 20 is held in its position within housing 12 by placing end 25 of strip unit 20 in base 13. Base 13 can be a stiff plastic structure adapted to end 19 of housing 12 which is rounded. Base 13 comprises a depression 21 adapted to end 25 of analysis strip unit 20. According to other embodiments no base is required and an analysis strip unit can be positioned within a housing of a diagnostic kit without a supporting base. Analysis strip unit 20 comprises a flow testing strip comprising of a receptacle element 24 for receiving samples to be analyzed, a sample wick 28 with a conjugate pad 30 for initiating the analyzed conjugated liquid, lateral flow strip membrane 22 for visually presenting the analysis results, and lateral flow absorbent wick 32 for directing and aiding the capillary action advancement of the analyzed liquid from sample wick 28. Receptacle element 24 is a receptacle cup shape liquid container fabricated from inert plastic or the like. Receptacle 24 comprises fluid solution 52 that is a reagent. Fluid solution 52 can be a buffer and/or an extraction liquid used for a sample inserted in receptacle 24. Thus, insertion of a sample to fluid solution 52 enables (as depicted below) the analysis initiating soon after sample wick 28 is dipped in fluid solution 52. Receptacle 24 is initially sealed with foil 26 that seals the receptacle and its liquid contents 52. Foil 26 can be fabricated from nylon or aluminum or any other material that substantially seals contents of receptacle 24. Furthermore, according to the present embodiment, foil 26 is a material that can be penetrated by sampling unit 11 as shown in FIGS. 4A, 4B. Receptacle 24 placed in base 13 is positioned on one end of analysis strip unit 20 and is adjacent to sample wick 28. Receptacle 24 further comprises opening 67 covered with foil 26. As shown in FIG. 4A sample wick 28 is juxtaposed to conjugate pad 30 at portion 51. Portion 50 of sample wick 28 is initially (i.e. prior to the initiation of the diagnosis) placed above foil 26 of receptacle 24. Conjugate pad 30 is attached to sample wick 28 and to flow membrane 22. Lateral flow membrane 22 provides chromatographic presentation of analytes due to the analysis of the fluid advancing in capillary action within membrane 22. The advancement of fluid from sample wick 28 and conjugate pad 30 through membrane 22 is enabled by flow absorbent wick 32 located in second end of strip unit 20.

Sampling unit 11 comprises sampling element 36 and elongated rod 38. Rod 38 is positioned adjacent to sampling element 36. Sampling element 38 is able to collect a sample by contacting a substance. Collecting of sample can be by absorbing a sample from a substance with a sampling unit 38. Sampling element 38 may be a sponge like swab, fibrous swab and the like. Sampling element 38 may be made of nylon, rayon, Dacron, cotton, a combination thereof and the like. Other embodiments can comprise other sampling units for collecting samples such as receptacle. Rod 38 is a flexible member used as an elongated handle for removing and inserting sampling unit 11 in housing 12. Rod 38 can be made of a plastic material and the like. Sampling unit 11 comprises further a plug 40 at its proximal end. Plug 40 can be fabricated from synthetic rubber and the like. Plug 40 encircles rod 38 and is fitted to the perimeter of open end 17 of housing 12. Thus, plug 40 substantially seals housing 12 when sampling unit 11 is fully inserted in the housing in both locations shown separately in FIGS. 1A, 3A. The sealing by plug 40 prevents external contamination of an inserted sample, sampling unit 11, or analysis strip unit 20. Alternatively, in other embodiments a plug can separate a housing section from the rest of housing. Thus, a section of housing comprising a sampling unit within diagnostic kit can separate a housing to two or more sections by a plug from its surroundings thus, preventing external contamination of a sample, sampling unit, and analysis strip unit.

Figure 2A:
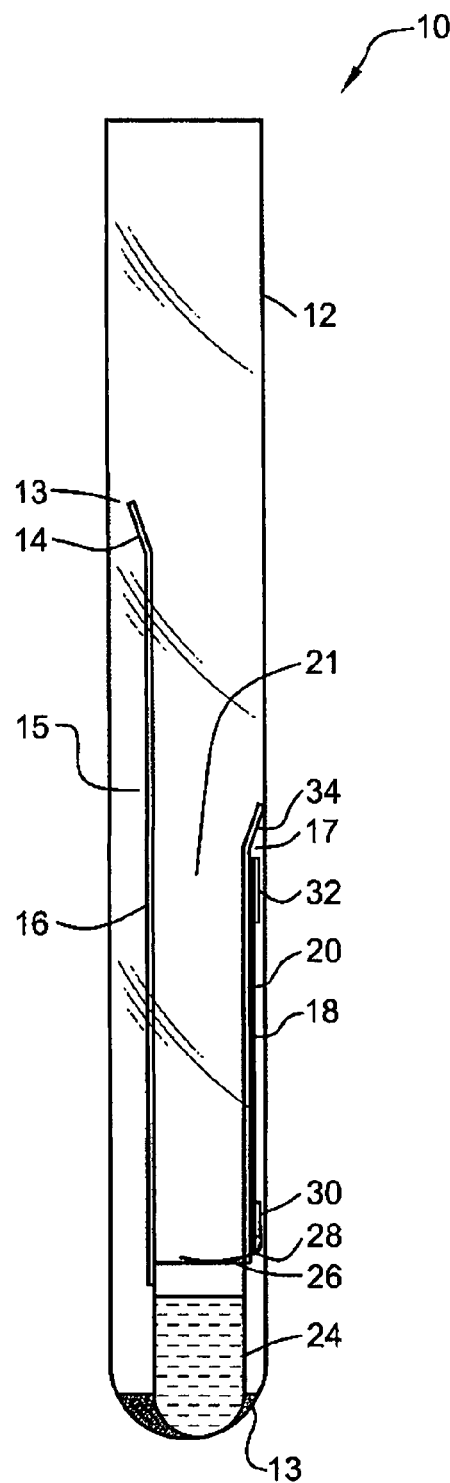
FIGS. 2A, 2B are front and side views, respectively, of a diagnostic kit according to the embodiment of FIG. 1A wherein the sampling unit is removed from the housing.
Figure 2B:
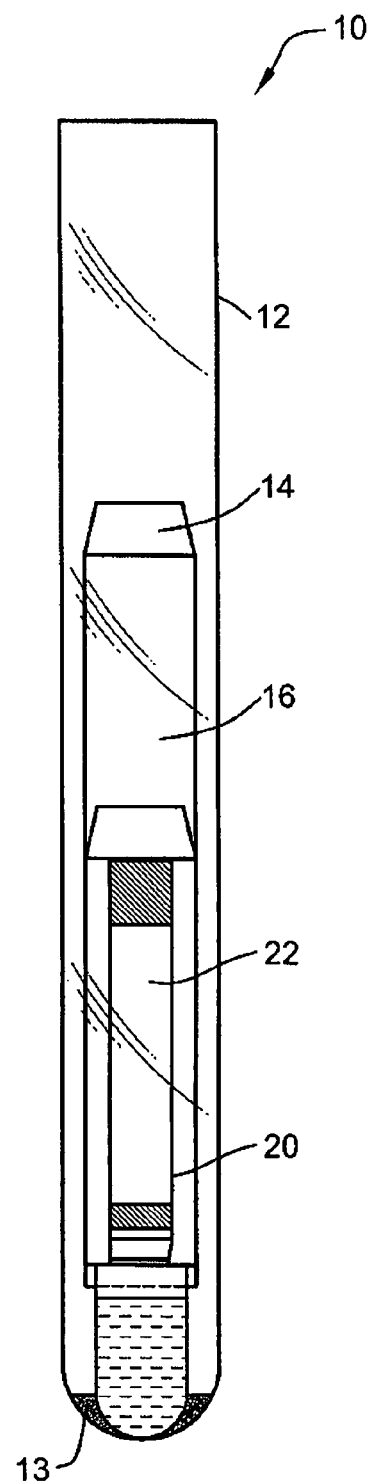
Figure 3A:
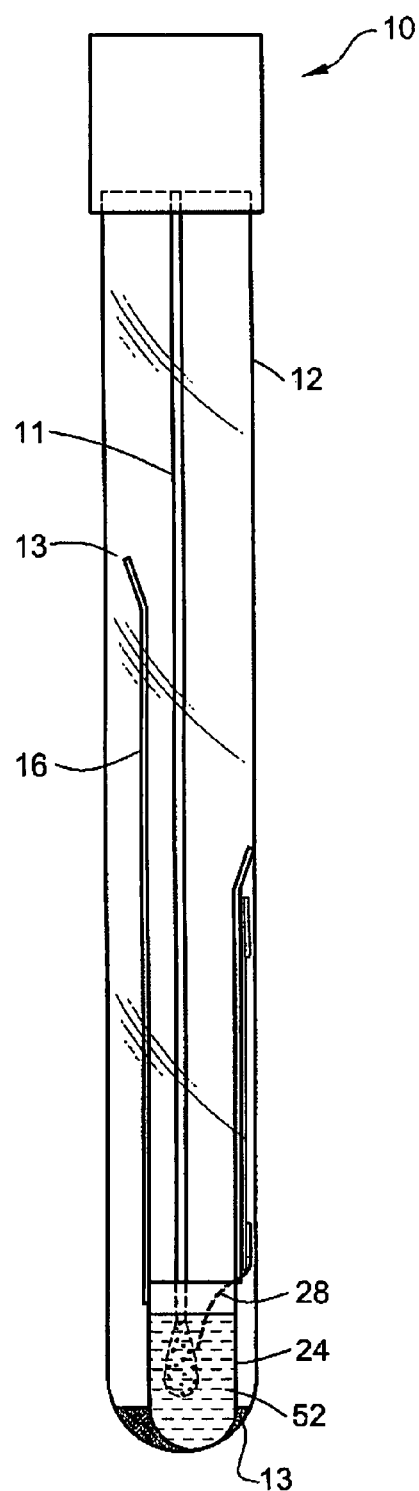
FIGS. 3A, 3B are front and side views, respectively, of a diagnostic kit according to the embodiment of FIG. 1A wherein the sampling unit is reentered the housing with sample.
Figure 3B:
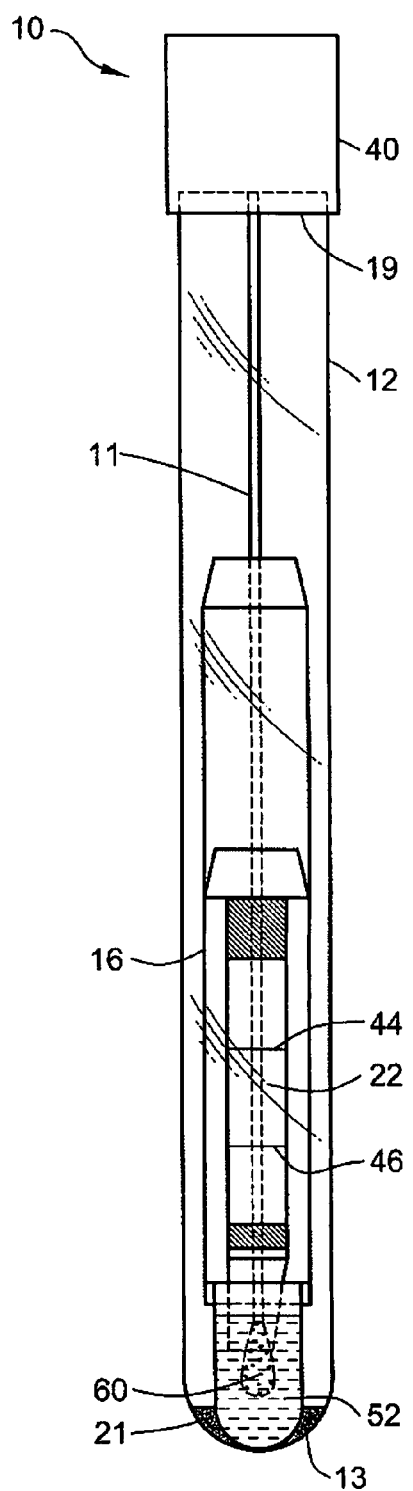

Diagnostic kit 10 provides a complete self contained kit. FIGS. 1A, 1B show the initial state of diagnostic kit 10. FIGS. 1A, 1B show analysis strip unit 20 positioned within housing 12. Additionally, diagnostic kit 10 is supplied with sampling unit 11. Plug 40 ensures the substantial sealing of housing 12. Thus, the initial state of diagnostic kit 10 provides a kit with all elements required to perform an analysis of a sample. FIGS. 2A, 2B show diagnostic 10 after sampling unit 11 is removed from housing 12. Sampling unit 11 is removed from housing 12 in order to collect a sample (not shown). Thus, analysis strip unit 20 remains within housing 12 ready to receive a sample and initiate its analysis. FIGS. 3A, 3B show sampling unit 11 re-entered housing 12 and placed in receptacle 24. As more clearly shown in FIGS. 4A, 4B sampling unit 11 upon re-entering housing 12 penetrates foil 26 and immerses the sampling unit approaching receptacle 24 is indicated by arrow 69. Concurrently with penetrating foil 26 sampling unit 11 drags and dips sample wick 28 in fluid solution 52. Consequently, placing sampling element 36 with action required. Analysis results are shown on membrane 22 shown in FIG. 3B with line 46 and control line 44.

Diagnostic kit 10 comprises further two opposite separators, first separator 16 and second separator 18. Separators 16, 18 are both flat elongated members with a bent proximal end. Separators 16, 18 have a width that is smaller than the width of housing 12. Separators 16, 18 aid defining opposite zones, 15, 17, respectively within housing 12. Separators 16, 18 are fabricated from inert and stiff materials with limited flexibility such as high density plastic materials and the like. Separator 16 defines zone 15 for initially placing sampling unit 11 (i.e. prior to the initiation of the diagnosis) as shown FIGS. 1A, 1B. Separator 16 is attached at one end to receptacle 24 thus affixing its position within housing 12. The proximal end of separator 16 comprises a bent section 14 leaving gap 13 between separator 16 and adjacent wall of housing 12. The width of sampling element 36 is wider than gap 13. Thus, once sampling unit 11 is removed from zone 15 as shown within FIGS. 2A, 2B it will not be returned to the zone 15 due to the width of gap 13. Separator 18, substantially placed opposite to separator 16 within housing 12, is attached at one end to receptacle 24 affixing its position within the housing. Attachment of separators 16, 18 to receptacle 24 can be by using durable glue, a clip, and the like or by welding. Separator 18 comprises a proximal bended end 34 having its tip placed adjacent to wall of housing 12. Thus, separator 18 defines zone 17 within housing 12. According to the present embodiment, analysis strip unit 20 with the exception of receptacle 24 and part of sample wick 28 (i.e. portion 50 of wick 28) is positioned within zone 17. As shown best in FIGS. 2A, 2B, the structure and position of separators 16, 18 create passage 21. Passage 21 dictates the route of sampling unit 11 reentering housing 12 after collecting a sample (i.e. sampling element 36 comprising sample 60 for analysis). Accordingly, FIGS. 3A, 3B demonstrate sampling unit 11 reentered housing 12. Passage 21 verifies that sampling element 36 with sample 60 will reach receptacle 24 and fluid solution 52. Furthermore, as depicted above, insertion of sampling unit 11 for analysis verifies substantial sealing of housing 12 by plug 40 and avoiding possible contamination within housing 12.

FIGS. 2A, 2B show housing 12 with analysis strip unit 20 after removing sampling unit 11 from diagnostic kit 10. Gap 13 does not provide reentering of sampling unit 11 and sampling element 36 into zone 15. Thus, sampling and using the diagnostic kit 10 comprises the following steps: removing sampling unit 11 from housing 12 from its initial position shown in FIGS. 1A, 1B. Sampling unit collects sample from a surface (e.g. vaginal surface, food remains on a table) not shown. Sampling unit 11 reenters housing 12 and navigated to receptacle 24. Accordingly, swab 36 drags sample wick 28 into receptacle 24 concurrently penetrating foil 26 and tearing it open. Thus, sample within swab 36 is immersed within fluid solution 52 and sample wick 28 is dipped within fluid solution 52. Consequently, analysis of sample 60 is initiated.

The present invention provides that a diagnostic kit can be provided with a sampling unit to a user. The diagnostic kit comprises an analysis strip unit and all reagents and buffer solution for performing an analysis. The sampling unit can be removed from the diagnostic kit for collecting a sample and after returning the sampling unit with a sample to the diagnostic kit for performing an analysis. A sample can be collected from any surface or location. Subsequent to collecting the sample the sample is inserted to the diagnostic kit and sample is immersed with a reagent or buffer solution within the diagnostic kit positioned adjacent to the analysis strip unit and a sample wick as disclosed above. Consequently, after immersing the sample and after the sample is dipped in the solution the analysis is initiated, thus using an analysis strip capillary forces force the transfer of substance analyzed along the strip.

Figure 5:
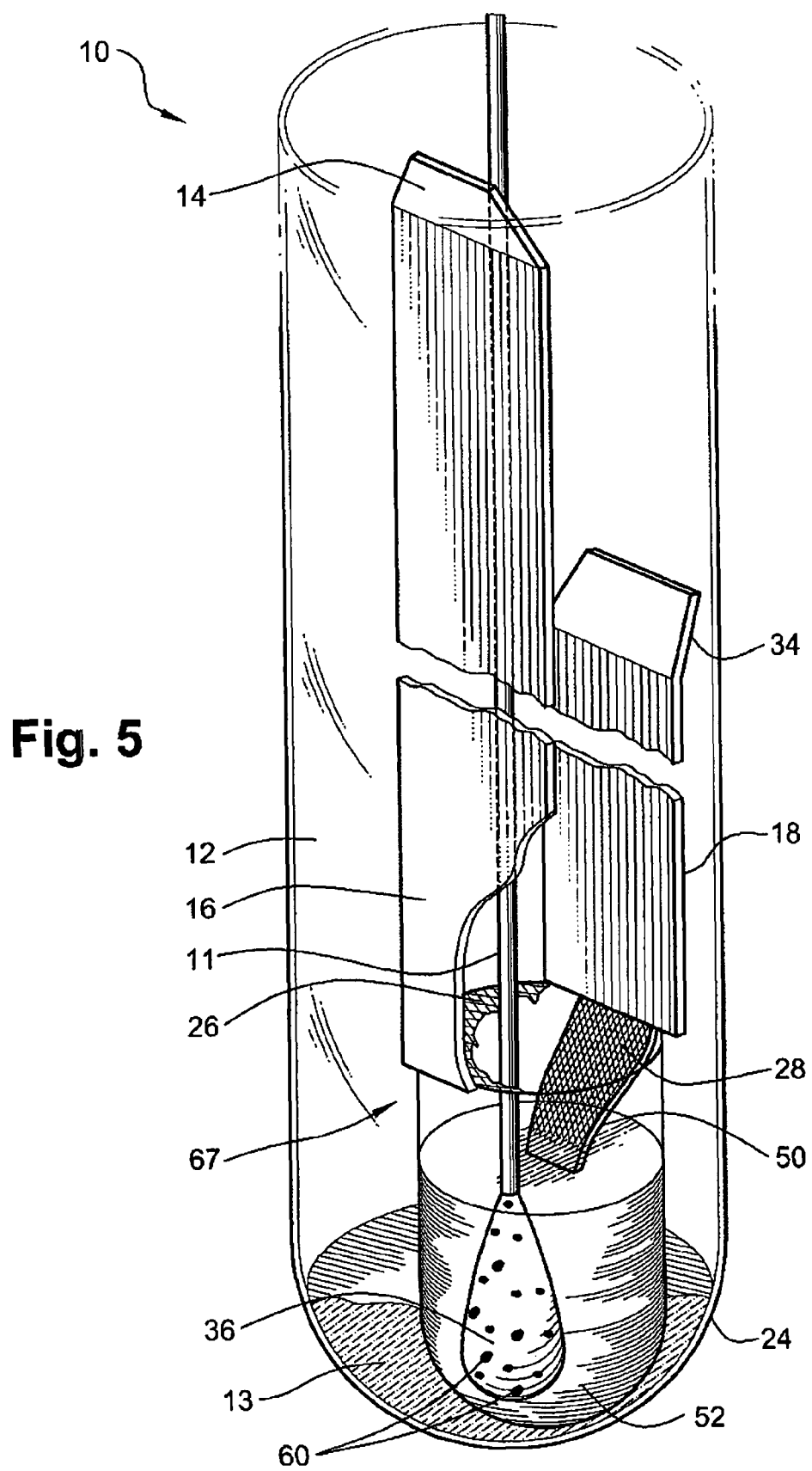
FIG. 5 is a perspective view of sampling unit placed within a receptacle.

FIG. 5 provides a further perspective view of sampling unit 11 and sampling element 36 inserted in receptacle 24. Sampling element 36 is shown with sample 60 after penetrating foil 26 and having pushed down portion 50 of sample wick 28. Thus, one end of portion 50 is dipped within fluid solution 52. Subsequently, to the insertion of sampling element 36 with sample 60 within fluid solution 52, sample 60 is immersed and/or reacts with reagent comprising fluid solution 52 forming a sample for analysis (not shown) within the solution 52 by analysis strip 20. Consequently, after portion 50 absorbs said sample for analysis from solution 52 analysis is begun.

The next examples provide some exemplary embodiments of the present invention as follows:

EXAMPLE 1

Preparation of Immunochromatography Lateral Flow Strip for Diagnosis of Candida Immunochromatography strip was prepared by assembly of different membranes, sequentially arranged on a non-absorbing clear plastic film with a release liner protected adhesive, serving as back laminate (ARcare 8876, Adhesive Research, Limerick, Ireland). The layers comprises a first sample pad (cellulose paper 2992 S&S), a second conjugate pad (Glass fiber filters Millipore, GFCP0010000) preimpregnated with gold conjugates, a chromatography membrane made of Nitrocellulose (Nitrocellulose HF18004, Millipore) and an absorbent pad (Gel blotting paper, S&S, GB003). The sample pad, conjugate pad and nitrocellulose are layered to form an overlapping there between, preferably of about 1 to 2 mm length.

A detection capture line is formed on top of the nitrocellulose membrane by plotting a solution of 1 mg/ml of Rabbit anti Candida polyclonal antibodies in 10 mM phosphate buffer pH 7.

The conjugate pad is made by soaking a glass fiber filter in a solution of colloidal gold conjugated to the same polyclonal antibodies anti-Candida that are used for the capture line. The conjugate coating solution comprise on 5% Trehalose in 50 mM Tris buffer. Following the soaking of the conjugate solution, the pad is dried overnight at 37° C., before assembly of the strip. The assembled card is cut into 4 mm strips.

EXAMPLE 2

Running of Test Strips with Candida Samples

The strips constructed as described in example 1 above, were tested for the presence of Candida antigens in cultures of different Candida species. Sample solutions were made by mixing 10 µl of culture with 50 µl running buffer composed of 0.5% PEG (PolyEthyleneGlycol-15000, Merck, 819003), 0.5% BSA (01200050, Seracare, Calif., USA), 0.1% Tween 20 (Sigma, P-5927), 0.1% MgCl2 (Merck 1200310) in TBS (Tris buffer saline) pH 7.8.

To start the test, 60 □l of sample solution was loaded onto the sample pad of the strip and. A Positive result appeared as a red line at the capture line within 1-15 min. Negative control (where no Candida present) didn't show any red line. The strips were observed up to 30 minutes.

The intensity of the signal was assigned "+" values (see Table 1) alternatively or in addition, the color can be detected and measured by an electro-optical instrument. The signal appearance time from the loading of the sample to the test strip and the intensity of the signal at 15 minutes are shown in the table. The results are summarized in following Table 1.

TABLE 1

| results obtained by the Candida test strip | |
| --- | --- |
| Culture (10 µl) + 50 µl buffer | Signal intensity after 15 minutes* |
| C. albicans $10^6$ cells/ml | ++++ |
| C. albicans $10^5$ cells/ml | +++ |
| C. albicans $10^4$ cells/ml | ++ |
| C. albicans $10^3$ cells/ml | + |

TABLE 1-continued

| results obtained by the Candida test strip | |
| --- | --- |
| Culture (10 µl) + 50 µl buffer | Signal intensity after 15 minutes* |
| C. glabrata $10^4$ cells/ml | +++ |
| C. krusei $10^4$ cells/ml | ++++ |
| C. tropicalis $10^4$ cells/ml | ++++ |
| L. plantarum $5 \times 10^6$ cells | − |
| Buffer | − |

*Relative signal intensity: Very strong (++++), strong (+++), medium (++), weak (+) and no signal (−).

EXAMPLE 3

Testing Clinical Samples in Candida Lateral Flow Strips 152 clinical samples were tested to evaluate the clinical relevance of the Candida test strip for the diagnosis of Vulvovaginal Candidiasis (VVC). Vaginal discharge samples were obtained from volunteers at the Genitourinary Infections unit of the Wolfson Medical Center, Holon, Israel. Vaginal discharges were collected by a physician using a sterile Nylon swab (552C, Copan, Italia). The swab heads (tips) were placed in 2 ml screw-cap tubes and kept at 4° C. until use. The vaginal swabs were washed by adding 300 µl of running buffer into the tube and by vortexing for 1 minute to elute the secretions from the swab and to achieve a homogenous sample. For each vaginal swab a diagnosis for Candida was done using wet mount microscopy and by culturing on Chromagar Candida Petri dish (HyLabs, Israel) for 48 h. From the 300 µl swab wash, 60 µl were taken for the test. The test was done as described above for culture samples.

Table 2 summarizes the result of 152 vaginal swabs washes that were diagnosed for VVC and tested with the Candida test strip.

TABLE 2

Vaginal samples (N = 152) diagnosed for Candida with culture and tested in the Candida lateral flow test.

| | | Candida culture | |
| --- | --- | --- | --- |
| | N = 152 | Positive | Negative |
| Candida Lateral flow test | Positive | 54 | 3 |
| | Negative | 6 | 89 |
| | Total | 60 | 92 |

The Sensitivity of the Candida Test Strip is 90% and Specificity 96%.

EXAMPLE 4

Preparation of Self Contained Diagnostic Swab for the Detection of Candida

A prototype of the self contained device was prepared by using a commercially available nylon swab in a transparent collection tube (Copan, Italia). The collection tube of the swab was used as the housing of the swab and detection system. A buffer reservoir was made of a 200 µl PCR tube, filled with 100 µl of the aforementioned running buffer. The filled tube was sealed with a 1 cm² saran. A Candida test strip, prepared as aforementioned, was attached to the edge of the tube, in a way that the sample pad was laid on top of the sealing saran (see FIG. 4b). The swab was removed from the collection tube and the buffer reservoir with the attached strip were inserted into the swab's collection tube, together with the swab.

EXAMPLE 5

Test of *Candida* Culture with the Self Contained Diagnostic Swab

The self contained diagnostic swab was tested culture of *Candida albicans*. The swab was pulled out of the tube, without taking out the buffer reservoir and strip, and was deep into a culture of *Candida albicans* for 10 sec. The swab was placed back into the collection tube and was pushed all the way into the buffer reservoir, through the sealing saran. Upon puncturing the seal, the buffer washed the swab tip, and fluid was contacted the sample pad and run into the strip. A Positive result appeared as a red line at the capture line within 1-15 min. Negative control (where no *Candida* present) didn't show any red line. The strips were observed up to 30 minutes.

The intensity of the signal at 15 minutes was assigned "+" values (see Table 2).

TABLE 2 results obtained by the self contained diagnostic swab for detection of *Candida*

| Culture | Signal intensity after 15 minutes |
|---|---|
| *C. albicans* $10^6$ cells/ml | ++++ |
| Negative culture | − |

According to other embodiments a receptacle at an end of analysis test strip is held tightly against an elastic body by a sampling unit tip placed adjacent to the receptacle positioned on the closed end of a housing. The elastic body is adjacent on the opposite side to the housing wall. Accordingly, after the sampling unit is removed from the housing the receptacle is moved away from the elastic body into the centre of the closed end of the housing. Thus, removal of sampling unit from housing dictates that upon re-entering of the sampling unit tip it will be placed within the receptacle sealed with a foil. Thus, similarly to the embodiment above the sampling unit penetrates the foil and dips a sample pad within the receptacle. Other embodiments can provide other sealing means to a receptacle as well as to the housing. Further embodiments can provide a self contained kit including separators that are not flat and are partly rounded and support a receptacle for inserting a sample. Further embodiments may not include opposite separators or separators at all. In still further exemplary embodiments may not include a sampling unit. Thus, a sample may be entered to a receptacle and the analysis can be initiated by the contact of the sample with a buffer reservoir positioned within a housing. In other exemplary embodiments initiation of analysis of a sample is done by vibrations of the housing. The vibrations causing a sample wick to contact the receptacle and commence the analysis. Other embodiment can provide that the analysis can be read by an optical reader connected to a microprocessor which shows the results on a display unit outside the housing of a diagnostic kit.

The person skilled in the art will appreciate that what has been shown is not limited to the description above. The person skilled in the art will appreciate that examples shown here above are in no way limiting and are shown to better and adequately describe the present invention. Those skilled in the art to which this invention pertains will appreciate the many modifications and other embodiments of the invention. Some other embodiments of the present invention provide use of other sizes of strips, and other shapes of strips. Further embodiments provide the use of more than one strip unit. Other embodiments can provide the use of optical microprocessor for presenting the results. It will be apparent that the present invention is not limited to the specific embodiments disclosed and those modifications and other embodiments are intended to be included within the scope of the invention. Although specific terms are employed herein, they are used in a generic and descriptive sense only and not for purposes of limitation. Persons skilled in the art will appreciate that the present invention is not limited to what has been particularly shown and described hereinabove. Rather the scope of the present invention is defined only by the claims, which follow.

The invention claimed is:

1. A self contained diagnostic kit for performing analysis of a specimen comprising:
   a tubular housing having a bottom end and an upper end;
   a sampling unit removably stored within the housing, the sampling unit comprising a swab mounted at one end of a rod for collecting said specimen;
   at least one test strip positioned substantially along a wall of the tubular housing, the test strip having a sample receiving end;
   at least one receptacle positioned at the bottom end of said tubular body, the at least one receptacle containing a fluid reagent selected for extracting said specimen from said swab, the receptacle having an upper opening sealed by a rupturable foil;
   a longitudinal passage extending between said upper end of the tubular housing and said upper opening of said receptacle;
   a flexible elongated wick having one end in fluid communication or integrally formed with the sampling receiving end of said at least one test strip and a second end bent above and adjacent to said rupturable foil, intersecting said longitudinal passage, such that when the sampling unit is inserted into said receptacle through said passage, said second end of the wick is pushed down into the receptacle, thereby forming a fluid communication between said at least one receptacle and said at least one test strip.

2. A self contained diagnostic kit for performing analysis of a specimen comprising:
   a tubular housing having a bottom end and an upper end;
   a separator that divides said tubular housing into a storage zone and an analysis zone;
   a sampling unit removably stored within said storage zone, the sampling unit comprises a swab mounted at one end of a rod for collecting said specimen;
   at least one test strip positioned within the analysis zone substantially along a wall of the tubular housing, the test strip having a sample receiving end;
   at least one receptacle positioned at the bottom end of said tubular housing, the at least one receptacle containing a fluid reagent selected for extracting said specimen from said swab, the receptacle having an upper opening sealed by a rupturable foil;
   a longitudinal passage extending between said upper end of the tubular housing and said upper opening of said receptacle; and
   a flexible elongated wick having one end in fluid communication or integrally formed with the sampling receiving end of said at least one test strip and a second end bent above and adjacent to said rupturable foil, intersecting said longitudinal passage, such that when the sampling unit is inserted into said receptacle through said passage, said second end of the wick is pushed down into the receptacle, thereby forming a fluid communication between said at least one receptacle and said at least one test strip.

3. The diagnostic kit of claim 2 wherein the sampling unit comprises a plug mounted substantially at a second end of said rod and wherein said plug is dimensioned to seal the upper end of the tubular housing.

4. The diagnostic kit of claim 2 wherein said separator is configured to prevent reinsertion of said sampling element into said storage zone.

5. The diagnostic kit of claim 2 wherein both the storage zone and the analysis zone open to the upper end of the tubular housing.

6. The diagnostic kit of claim 2 wherein the test strip comprises a detection zone where a visible signal indicative of test results is formed, and wherein the tubular housing comprises a transparent area through which said detection zone can be viewed.

7. The diagnostic kit of claim 2 wherein said fluid reagent comprises a buffer.

8. The diagnostic kit of claim 2 wherein said fluid reagent comprises an extraction fluid.

9. A method for performing analysis of a specimen, the method comprising:

collecting said specimen by means of a sampling unit comprising a swab mounted at one end of a rod;

providing a diagnostic device comprising:
- a tubular housing having a bottom end and an upper end;
- at least one test strip positioned inside the housing substantially along a wall thereof, the test strip having a sample receiving end;
- at least one receptacle positioned at the bottom end of said tubular body, the at least one receptacle containing a fluid reagent selected to extract said specimen, the receptacle having an upper opening sealed by a rupturable foil;
- a longitudinal passage extending between said upper end of the tubular housing and said upper opening of said receptacle; and
- a flexible elongated wick having one end in fluid communication or integrally formed with the sampling receiving end of said at least one test strip and a second end bent above and adjacent to said rupturable foil, intersecting said longitudinal passage;

inserting said sampling unit through said longitudinal passage;

rupturing said rupturable foil by said one end of said sampling unit to enter said swab into said fluid reagent, thereby said specimen is extracted into said fluid reagent and said wick is partially dipped into said fluid reagent to form a fluid communication between said at least one receptacle and said at least one test strip.

* * * * *